(12) United States Patent
Kusch

(10) Patent No.: US 6,795,571 B2
(45) Date of Patent: Sep. 21, 2004

(54) SYSTEM AND METHOD FOR GENERATING AN IMAGE DATASET

(75) Inventor: Jochen Kusch, Effeltrich (DE)

(73) Assignee: Siemens Aktiengesellschaft, Münich (DE)

( * ) Notice: Subject to any disclaimer, the term of this patent is extended or adjusted under 35 U.S.C. 154(b) by 605 days.

(21) Appl. No.: 09/823,110

(22) Filed: Mar. 30, 2001

(65) Prior Publication Data

US 2002/0018588 A1 Feb. 14, 2002

(30) Foreign Application Priority Data

Mar. 30, 2000 (DE) .......................................... 100 15 815

(51) Int. Cl.⁷ ................................................ G06K 9/00
(52) U.S. Cl. ..................................................... 382/131
(58) Field of Search ............................... 382/128, 130, 382/131, 132, 154; 600/407, 410, 417, 425, 166; 290/363.04, 583, 370.09, 559.05; 378/4, 20, 21, 62; 356/390; 359/458; 348/47; 399/300; 700/57, 58, 59, 64, 66, 135; 250/363.04, 583, 370.09, 559.05, 208.6

(56) References Cited

U.S. PATENT DOCUMENTS 5,368,032 A * 11/1994 Cline et al. ................. 600/411
6,483,948 B1 * 11/2002 Spink et al. ................. 382/255
6,662,036 B2 * 12/2003 Cosman ....................... 600/411
2002/0035864 A1 * 3/2002 Paltieli et al. ............... 73/1.01

FOREIGN PATENT DOCUMENTS

DE  OS 40 21 102    1/1991    ........... A61B/8/13
WO  WO 96/39939    12/1996    ........... A61B/8/08

OTHER PUBLICATIONS

"Lexikon der Computergrafik und Bildverarbeitugn," Iwainsky et al., (1994) pp. 31–32.

* cited by examiner

Primary Examiner—Andrew W. Johns
Assistant Examiner—Shervin Nakhjavan
(74) Attorney, Agent, or Firm—Schiff Hardin LLP

(57) ABSTRACT

In a system and a method for generating an image dataset that contains superimposed or fused image data, a first system for the acquisition of a first image dataset of a subject and a second system for the acquisition of a second image dataset of the subject are provided that are different from each other. With a navigation system, the positions of the first and the second systems in the acquisition of the image datasets are determined, with reference to which the attitudes of the two image datasets in space can be determined, so that the two image datasets can be superimposed on one another or fused with one another.

14 Claims, 1 Drawing Sheet

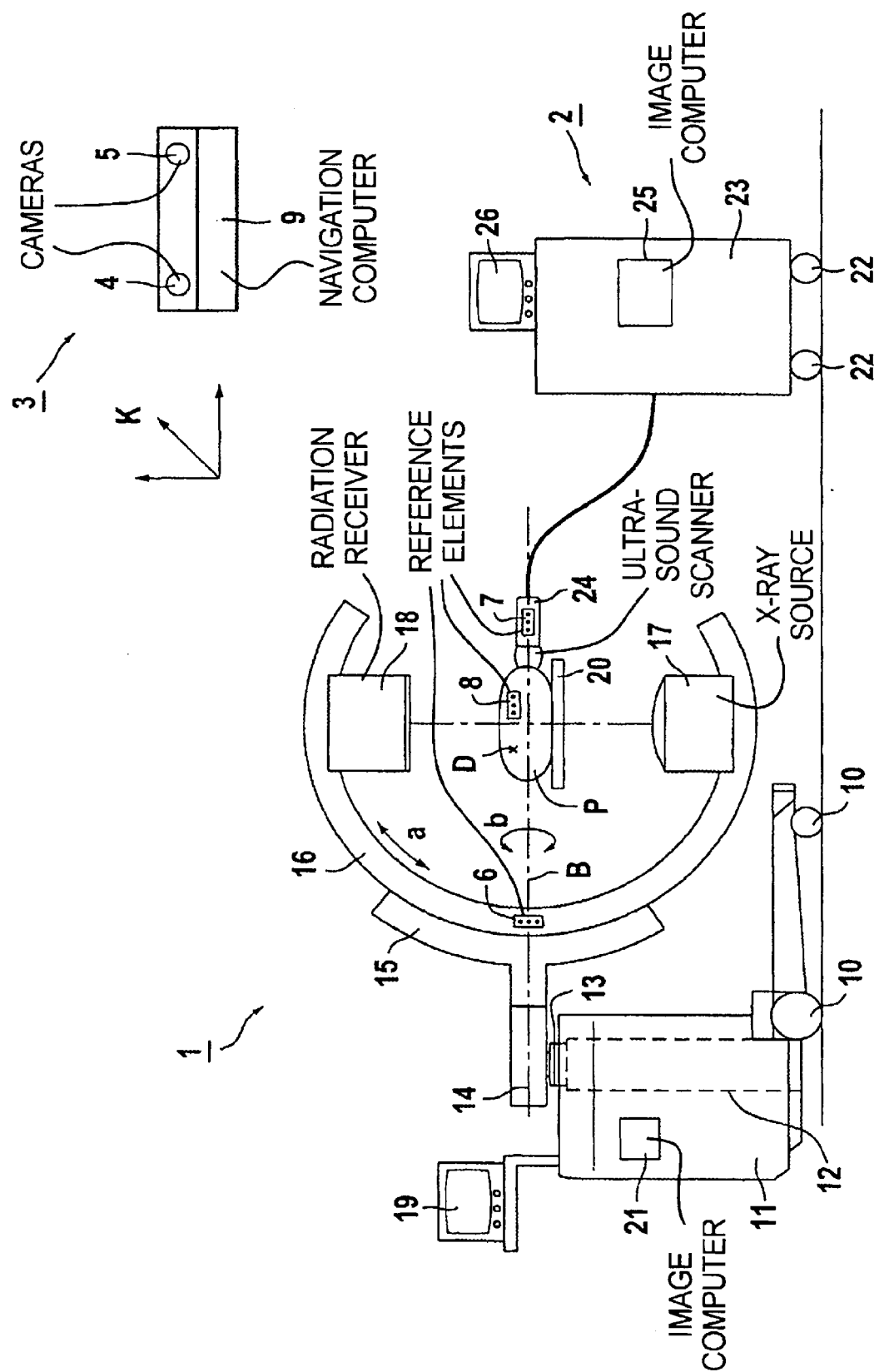

SYSTEM AND METHOD FOR GENERATING AN IMAGE DATASET

BACKGROUND OF THE INVENTION

1. Field of the Invention

The present invention is directed to a system and to a method for generating an image dataset that contains superimposed or fused image data.

2. Description of the Prior Art

Various imaging modalities can be utilized for acquiring image data of an object, particularly from the inside of the object. The selection of the imaging modality ensues dependent on the subject to be examined or, if the object is a living subject, dependent on the tissue to be examined. It is especially advantageous when 3D image datasets of the subject to be examined or tissue to be examined can be acquired with the imaging modality. Diagnostically useful 3D images can be capable of being produced therefrom.

In medicine, x-ray computed tomography systems and magnetic resonance systems are usually employed for acquiring 3D image datasets of bone structures and of soft tissue. These 3D image datasets are of assistance in diagnostics since fractures as well as hemorrhages or other soft tissue injuries can be recognized. Moreover, 3D image datasets of bone structures can be acquired in conventional x-ray technology, for example with permanently installed or portable C-arm x-ray devices, and 3D image datasets of soft tissue can be acquired with ultrasound devices.

Nonetheless, it is disadvantageous that either only bone structures or only soft tissue can be recognized well as a rule in the images generated with the devices employing x-radiation or ultrasound.

German OS 40 21 102, however, discloses a medical diagnostic installation having two integrated, imaging systems, one being an x-ray system and the other being an ultrasound system. The surface or spatial allocation of an ultrasound tomogram generated with the ultrasound system to an x-ray image generated with the x-ray system is determined with the assistance of position sensors in order to be able to mix the ultrasound tomogram into the x-ray image. For this purpose, however, the x-ray system and the ultrasound system must be arranged in a defined way relative to one another in order to be able to produce a relationship between the image data of the x-ray system and of the ultrasound system.

The section "Bildrektifikation" in "Lexikon der Computergrafik und Bildverarbeitung" by Iwainsky, A. and Wilhelmi W., Vieweg Verlagsgesellschaft, 1994, pages 31, 32 describes methods for the geometrical and radiometrical correction of picture elements for the purpose of matching two images. Two methods for the geometrical correction are described, one being directed to the calculation of two-dimensional correction polynomials of the order k, and the other being directed to a perspective transformation method.

PCT Application WO 96/39939 discloses a method and a system for correlation of ultrasound image data with x-ray image data.

An object of the present invention is to provide a system and a method for generating images of a subject which allow the images to be generated in a simple way, the images containing information acquired with two imaging modalities that are different from one another.

According to the invention, this object is achieved in a system for generating an image dataset that contains superimposed or fused image data, having a first image acquisition system for acquiring a first image dataset of a subject, a second system different from the first for acquiring a second image dataset of the subject, a navigation system for determining the positions of the first and the second systems in the acquisition of the image datasets, a unit for determining the position of the first image dataset acquired with the first system and the position of the second image dataset acquired with the second system, and a unit for superimposition and fusion of the image data of the first image dataset and the second image dataset. Inventively, the positions or the attitudes of the image datasets in space generated with the first and second systems can be determined with a computational unit, for example with a computer, from the identified positions that the first and the second systems assumed in the acquisition of the first and second image dataset. The knowledge of the attitudes of the image datasets acquired with the first and second systems, finally, allows these to be superimposed on one another or allows these to be fused with one another to form an image dataset. Finally, images that contain information that were acquired with two different imaging modalities are acquired from the image dataset comprising superimposed or fused image data. A navigation system is provided for determining the positions of the first and the second systems in the acquisition of the image datasets. The navigation system has contact-free sensors for determining the position of a subject in space. For example, the navigation system can be a known optical navigation system, an electromagnetic navigation system, a navigation system operating with acoustic waves, for example ultrasound, or some other known navigation system.

In one embodiment of the invention, the attitudes and position of the subject also can be identified in space with the navigation system. The determination of the attitudes and positions of the subject during the acquisition of the image datasets maybe required under certain circumstances when the subject to be examined is not inmmovably fixed during the acquisition of the image datasets, or when the acquisition of the two image datasets does not ensue simultaneously and the subject moves or is moved between the acquisition of the two image datasets. Accordingly, the subject is in a different attitude in the image dataset acquired with the first system than in the image dataset acquired with the second system. The two image datasets therefore cannot be superimposed on one another without further difficulty or fused with one another. Due to the acquisition of the movement of the subject, it is ultimately possible to adapt the two acquired image datasets to one another taking the movements of the subject into consideration such that a superimposition or fusion of the two datasets can ensue.

In a preferred embodiment of the invention, 3D image datasets can be acquired with the first system and/or with the second system for acquiring the respective image dataset. The first system can be an x-ray system, preferably a C-arm x-ray system, and the second system can be an ultrasound system. In this way, image datasets of life forms can be produced from which images can be reconstructed wherein bone structures as well as soft tissue are presented. The advantage of employing a C-arm x-ray system and an ultrasound system for generating the two image datasets to be superimposed on one another, or the two image datasets to be fused with one another, lies in the relatively economic production of the image datasets compared to the acquisition of datasets with an x-ray computer tomography apparatus or a magnetic resonance apparatus. Moreover, the examination subject need not be repositioned in the acquisition of the image datasets with a C-arm x-ray system and an ultrasound system, as is usually the case given acquisition of the image datasets with an x-ray computed tomography apparatus and a magnetic resonance apparatus.

The above object also is achieved in a method for generating an image dataset that contains superimposed or fused image data having the following method steps:

a) Acquisition of a first image dataset of a subject with a first system for acquiring image data;

b) Acquisition of a second image dataset of the subject with a second system for acquiring image data different from the first system;

c) Determining the positions of the first and the second systems in the acquisition of the image datasets with the navigation system d) Determining the position of the first image dataset acquired with the first system and the position of the second image dataset acquired with the second system; and e) Superimposition or fusion of the image data of the first image dataset and the second image dataset.

The positions of the first and second systems in the acquisition of the image datasets can be determined in a simple way with the navigation system. Proceeding from the identified positions of the first and second systems, the positions of the image datasets acquired with the first and second systems also can be identified, so that these can be superimposed on one another or fused with one another in a simple way.

DESCRIPTION OF THE DRAWINGS

The single FIGURE shows an exemplary embodiment of the invention having a navigation system for the implementation of the inventive method.

DESCRIPTION OF THE PREFERRED EMBODIMENTS

The invention system shown in the FIGURE is a medical system. The medical system has a first system for acquiring a first image dataset in the form of a portable C-arm x-ray apparatus 1 and a second system for acquiring a second image dataset in the form of an ultrasound device 2. The medical system also has a navigation system for positional identification. This navigation system is an optical navigation system 3 in the case of the exemplary embodiment, having a camera system with two cameras 4, 5, having reference elements 6 through 8 that can be attached to subjects whose positions are to be acquired. The elements 6 through 8 can be registered by the cameras 4, 5. The navigation system further has a navigation computer 9.

The C-arm x-ray apparatus 1 has an apparatus carriage 11 movable on wheels 10 and a lifting mechanism 12 (only schematically indicated in the FIGURE) having a column 13. A holder 14, at which a holding mechanism 15 for a C-arm 16 is arranged, is secured to the column 13. An x-ray source 17 which emits a cone-shaped x-ray beam and an x-ray receiver 18 are arranged at the C-arm 16 opposite one another. In the exemplary embodiment, the x-ray receiver 18 is a known solid-state detector. The x-ray receiver 18, however, also can be an x-ray image intensifier, but a solid-state detector has the advantage over the x-ray image intensifier of supplying x-ray images that are geometrically distortion-free. The x-ray image acquired with the receiver 18 can be displayed on a display 19 in a known way.

The C-arm 16 is motor-adjustable around its pivot point D along its circumference in the holding device 15 (see the double arrow a, orbital motion). The C-arm 16 together with the holding device 15 also can be motor-pivoted around an axis B that proceeds substantially horizontally through the holder part 14, the holding device 15 and the C-arm 16 (see the double arrow b, angulation movement).

The C-arm x-ray apparatus 1 shown in the FIGURE allows 3D image datasets of body parts of a patient P borne on a patient support 20 (schematically indicated in the FIGURE ) to be produced, various 3D images of a body part of the patient P being able to be reconstructed therefrom. For producing a 3D image dataset and for producing 3D images, an image computer 21 is provided in the exemplary embodiment. The computer 20 is provided in the apparatus carriage 11 of the C-arm x-ray apparatus 1 and is connected (in a way that is not shown) to the solid-state detector serving as the radiation receiver 18 and to the display 19. The image computer 21 is operated such that 3D images can be reconstructed in a known way from the 2D projections registered with the x-ray system formed by the x-ray source 17 and the solid-state detector. The 2D projections of the body part of the patient P to be displayed in a 3D image are acquired given motorized adjustment of the C-arm 16 along its circumference around its pivot point D or given a motorized pivoting of the C-arm 16 around its angulation axis B.

The ultrasound apparatus 2 has an apparatus carriage 23 movable on wheels 22 as well as an ultrasound scanner 24 that can be conducted over the body surface of the patient P. The image data acquired with the ultrasound scanner 24 from the inside of the body of the patient P are supplied to an image computer 25 that is arranged in the apparatus carriage 23 and connected to the ultrasound scanner 24. The image computer 25 displays the ultrasound images acquired from the ultrasound data on a display 26 of the ultrasound apparatus 2. 3D image datasets of body parts of the patient P also can be acquired with the ultrasound apparatus 2. Such a 3D image dataset is produced in a known way from a number of ultrasound tomograms registered from different directions and forms the basis for the reconstruction of various 3D ultrasound images.

For producing an image dataset that contains image data of a 3D image dataset acquired with the C-arm x-ray apparatus 1, and image data of a 3D image set acquired with the ultrasound apparatus 2, a 3D image dataset of a body part of the patient P to be examined is acquired with the x-ray apparatus 1 and a 3D image dataset thereof is acquired with the ultrasound apparatus. The positions of the x-ray system and of the ultrasound scanner 24 are identified at the times of the exposure of the 2D projections with the C-arm x-ray apparatus 1 as well as at the times of the exposures of the ultrasound tomograms with the ultrasound apparatus 2, being determined with the assistance of the navigation system 3. To this end, the reference elements 6 and 7 of the navigation system 3 are arranged at the x-ray system, at the C-arm 16 of the x-ray apparatus 1 in the exemplary embodiment, and at the ultrasound scanner 24. These reference elements 6 and 7 allow the positions of the x-ray system and of the ultrasound scanner 24 to be identified with reference to an arbitrary selectable reference coordinate system K.

The position determination ensues with the navigation computer 9 that interprets the images of the x-ray system provided with the reference element 6 registered by the cameras 4, 5 and interprets the images of the ultrasound scanner 24 provided with the reference element 7 during the registration of the 2D projections or of the ultrasound tomograms. The attitude of the 3D image dataset generated from the 2D projections in the reference coordinate system K also can be identified on the basis of the identified positions of the x-ray system in the 2D projections, since the attitude of the pivot point D of the C-arm 16 as well as the attitude of the axis B are known on the basis of the known design of the C-arm x-ray apparatus, and since the x-ray source 17 and the radiation receiver 18 are arranged at the C-arm 16 in a defined way, i.e. in a geometrically identifiable and known way. The attitude of the 3D image dataset generated from the 2D ultrasound tomograms also can be determined on the basis of the identified positions of the ultrasound scanner in the acquisition of the ultrasound tomograms, in the reference coordinate system K on the basis of the registration parameters that are known in the registration of the 2D ultrasound tomograrms.

Since both the attitude of the 3D image dataset acquired with the C-arm x-ray apparatus 1 as well as the attitude of the 3D image dataset acquired with the ultrasound apparatus 2 can be identified in the reference coordinate system K, the two 3D image datasets can be superimposed on one another or fused with one another. The determination of the attitudes of the image datasets as well as the superimposition or the fusion of the two 3D image datasets preferably ensues with the image computer 21 of the C-arm x-ray apparatus 1 or with the image computer 25 of the ultrasound apparatus 2. When, for example, the image computer 21 of the C-arm x-ray apparatus 1 is utilized for the determination of the attitudes of the image datasets as well as for the superimposition or fusion of the 3D image datasets, then this—via connecting lines that are not shown in detail in the FIGURE—receives all required data from the navigation computer 9 of the navigation system 3 as well as from the image computer 25 of the ultrasound apparatus 2. 3D images of the body part of the patient P to be examined that contain both information about bone structures as well as information about soft tissue can be subsequently produced from the generated image dataset that contains superimposed or fused image data. The images can be displayed in known way, for example on a display 19 of the C-arm x-ray apparatus 1.

If the registration of the 2D projections with the C-arm x-ray apparatus 1 and the registration of the ultrasound tomograms with the ultrasound apparatus 2 does not ensue simultaneously, or when the patient P is not fixed on the patient support 20 so as to preclude movement between the image exposures, the movement of the patient P is preferably acquired with the navigation system 3. The reference element 8 is attached to the patient P for this purpose in the exemplary embodiment. By acquiring the movement of the patient P by registering the reference element 8, it becomes possible to match image datasets to one another that were registered at different attitudes of the patient P with the C-arm x-ray apparatus 1 and with the ultrasound apparatus 2, with the movements of the patient P between the acquisition of the two image datasets being taken into consideration. This allows bone structures and soft tissue to be presented in the correct allocation to one another after the image superimposition or image fusion even given movement on the part of the patient P between the acquisition of the two image datasets.

In the superimposition or the fusion of the two image datasets acquired with a C-arm x-ray apparatus 1 and with the ultrasound apparatus 2, it will usually be necessary to adapt the image datasets to one another in terms of their structure as well. This can ensue, for example, so that the 3D image sets acquired with the C-arm x-ray apparatus 1 or the 3D image dataset acquired with the ultrasound apparatus 2 are both scaled such that both 3D image datasets have the same number of voxels per volume unit, and thus, a superimposition or fusion of the voxels is possible. Such a calibration, which can ensue on a one-time basis or cyclically as warranted, is usually undertaken after the registration of the 3D image datasets, by the superimposition or fusion computer, the image computer 21 of the C-arm x-ray apparatus 1 in the present case.

Such a calibration, however, can alternatively ensue with the assistance of a calibration phantom (not shown in detail) before the actual subject measurement. The calibration phantom has marks for this purpose that can be imaged both in x-ray images as well as in the ultrasound images. The as-needed adaptation, for example the scaling, of the image dataset or datasets ultimately can be determined and stored on the basis of the marks of the calibration phantom imaged in the image dataset acquired with the x-ray apparatus 1 and imaged in the image dataset acquired with the ultrasound apparatus 2. The adaptation is determined and stored in order, in the subject measurement, to enable a superimposition or fusion of the image dataset generated with the x-ray apparatus 1 and of the image dataset generated with the ultrasound apparatus 2 in such a way that bone structures and soft tissue are portrayed in the correct allocation relative to one another following the image superimposition or image fusion.

The correction of one or both image datasets determined by the calibration need not necessarily be scaling. Alternatively, only corrections at edge regions or of other regions of the image datasets could be necessary.

The superimposition or fusion of the 3D image datasets, moreover, need not necessarily be undertaken by the image computer21 of the C-arm x-ray apparatus 1 or by the image computer 25 of the ultrasound apparatus 2. Alternatively, a computer that is separately provided for this purpose can be present, the image computers 21, 25 of the x-ray apparatus and of the ultrasound apparatus 2 as well as the navigation computer 3 being connected thereto.

Differing from the exemplary embodiment described herein, the navigation system 3 need not necessarily be an optical navigation system. The navigation system can be a navigation system operating electromagnetically or with ultrasound waves or can be some other known navigation system that operates in non-contacting fashion for identifying the position system and for identifying the position of a subject.

Further, the present invention is not limited to the fusion or superimposition of 3D image datasets; rather, 2D image datasets or 2D and 3D image datasets that were produced with imaging modalities different from one another can be superimposed on one another or fused with one another.

The imaging modalities need not necessarily be a C-arm x-ray apparatus 1 and an ultrasound apparatus 2.

The invention was described above with reference to the example of a medical system, but is not limited to the field of medicine.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A system for generating an image dataset, comprising:
   a first system for acquiring a first image dataset of a subject;
   a second system, different from said first system, for acquiring a second image dataset of said subject;

a navigation system for determining first position information comprising respective positions of said first system during acquisition of said first image dataset and second system during acquisition of said second image dataset;

an image position determining system which generates second position information comprising a position of said first image dataset and a position of said second image dataset; and a combining unit for combining said first image dataset and said second image dataset in a combining operation selected from the group consisting of superimposition and fusion, dependent on said first position information and said second position information.

2. A system as claimed in claim 1, wherein said first position information further comprises an orientation of said subject during acquisition of said first image dataset and during acquisition of said second image dataset.

3. A system as claimed in claim 1, wherein said first system acquires a 3D image dataset as said first image dataset.

4. A system as claimed in claim 1, wherein said second system acquires a 3D image dataset as said second image dataset.

5. A system as claimed in claim 1, wherein said first system is an x-ray system.

6. A system as claimed in claim 1, wherein said second system is an ultrasound system.

7. A system as claimed in claim 1, wherein said first system acquires a first medical image dataset as said first image dataset and wherein said second system acquires a second medical image dataset as said second image dataset, and wherein said combining superimposes and fuses said first medical image dataset and said second medical image dataset to produce a medical diagnostic image.

8. A method for generating an image dataset, comprising the steps of:

acquiring a first image dataset of a subject with a first image acquisition system;

acquiring a second image dataset of said subject with a second image acquisition system which is different from said first image acquisition system;

determining respective positions of said first image acquisition system during acquisition of said first image dataset and of said second image acquisition system during acquisition of said second image dataset with a navigation system, thereby obtaining first position information;

determining a position of said first image dataset and a position of said second image dataset, thereby obtaining second position information; and combining said first image dataset and said second image dataset in a combining operation selected from the group consisting of superimposition and fusion, dependent on said first position information and said second position information.

9. A method as claimed in claim 8, comprising the additional step of identifying an orientation of said subject during acquisition of said first image dataset and during acquisition of said second image dataset, and including said orientation of said subject and said first position information.

10. A method as claimed in claim 9, comprising identifying the orientation of said subject using said navigation system.

11. A method as claimed in claim 8, comprising acquiring a 3D image dataset with said first image acquisition system as said first image dataset.

12. A method as claimed in claim 8, comprising acquiring a 3D image dataset with said second image acquisition system as said second image dataset.

13. A method as claimed in claim 8, comprising employing an x-ray system as said first image acquisition system.

14. A method as claimed in claim 8, comprising employing an ultrasound system as said second image acquisition system.

* * * * *